United States Patent [19]
Thornton et al.

[11] Patent Number: 5,246,450
[45] Date of Patent: Sep. 21, 1993

[54] HIGH CAPACITY MEDICAL CLIP FEEDING AND DISPENSING MECHANISM

[75] Inventors: Curtis W. Thornton, Cary; Harold G. Carruthers, Durham, both of N.C.

[73] Assignee: Edward Weck Incorporated, Princeton, N.J.

[21] Appl. No.: 849,165

[22] Filed: Mar. 10, 1992

[51] Int. Cl.$^5$ ............................................. A61B 17/00
[52] U.S. Cl. ................................. 606/143; 606/142; 227/901
[58] Field of Search ............... 606/139, 142, 143, 151; 227/901

[56] References Cited

U.S. PATENT DOCUMENTS

| | | |
|---|---|---|
| 3,307,389 | 3/1967 | Rose et al. ............... 606/143 |
| 4,296,751 | 10/1981 | Blake, III et al. ........... 606/143 |
| 4,375,866 | 3/1983 | Giersch et al. ............. 606/143 |
| 4,637,395 | 1/1987 | Caspar et al. .............. 606/143 |
| 4,662,555 | 5/1987 | Thornton . | |
| 4,674,504 | 6/1987 | Klieman et al. ............ 606/143 |
| 4,712,549 | 12/1987 | Peters et al. ............... 606/143 |
| 4,821,721 | 4/1989 | Chin et al. ................ 606/143 |
| 4,934,364 | 6/1990 | Green ...................... 606/143 |
| 4,971,198 | 11/1990 | Mericle . | |
| 5,035,692 | 7/1991 | Lyon et al. ................ 606/143 |
| 5,049,152 | 9/1991 | Simon et al. .............. 606/143 |
| 5,084,057 | 1/1992 | Green et al. .............. 606/143 |

Primary Examiner—Stephen C. Pellegrino
Assistant Examiner—Jeffrey A. Schmidt
Attorney, Agent, or Firm—Rosenblatt & Associates

[57] ABSTRACT

The present invention provides a means for applying a substantially constant force to move clips in queue within an applicator, as well as means for more effectively dispensing the endmost clip from a column of abrasive clips within an applicator. The constant force means generally comprises a constant force spring which is movably secured at both ends within a chamber in the applicator such that the pressure exerted between the ends of the constant force spring forces the clips in queue toward the jaws of the applicator. The dispensing means generally comprises a spring that applies sufficient pressure against the endmost clip in a column of abrasive clips to dispense the endmost clip from the column while preventing the next endmost clip from being dispensed until after the endmost clip has been forced into the jaws of the applicator and applied.

2 Claims, 3 Drawing Sheets

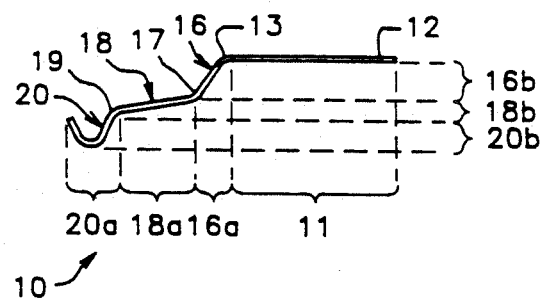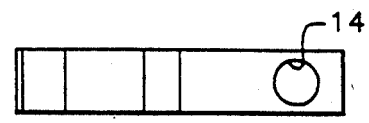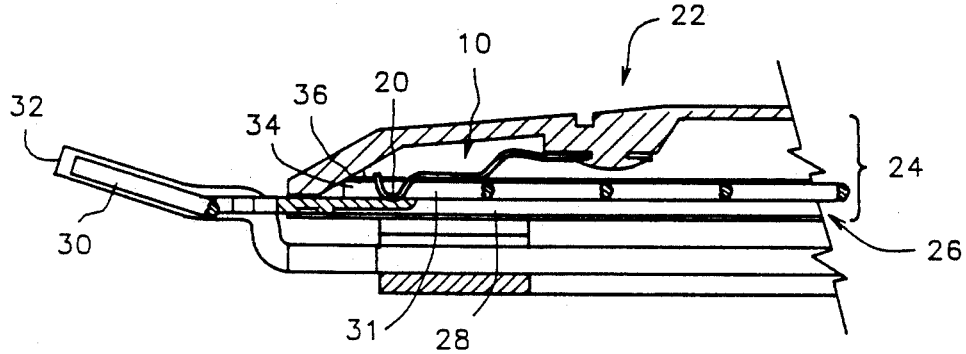
FIG. 3
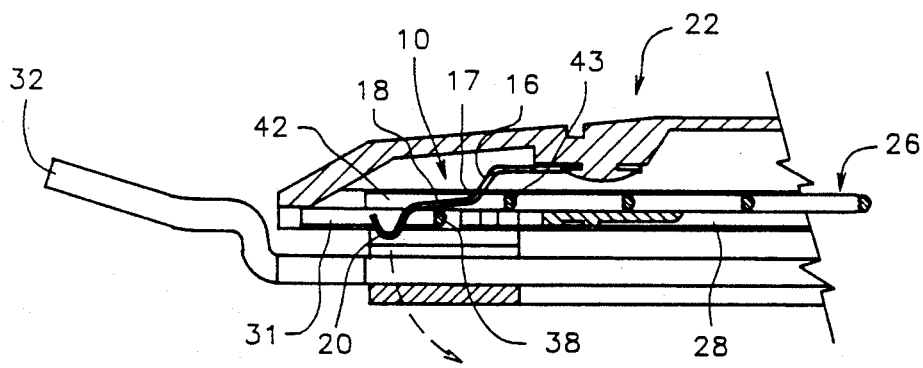
FIG. 4
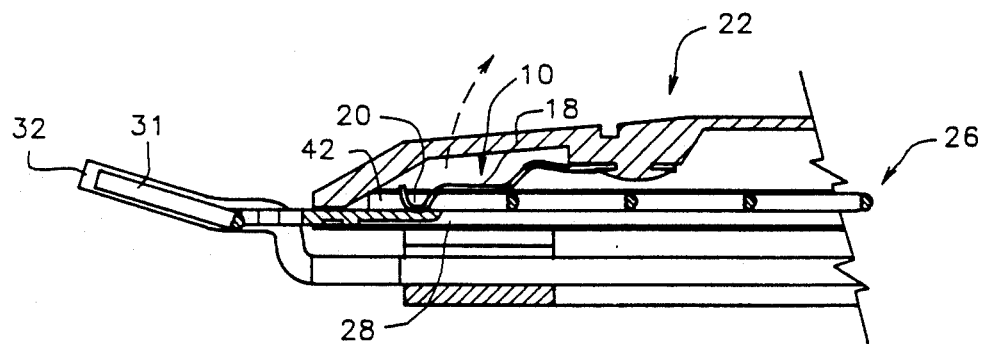
FIG. 5

HIGH CAPACITY MEDICAL CLIP FEEDING AND DISPENSING MECHANISM

BACKGROUND OF THE INVENTION

Field of the Invention

Hemostatic clips and surgical staplers have been used increasingly in recent years to supplant prior art techniques used to suture and close wounds or to tie off blood vessels during surgery or other traumatic medical care. Hemostatic clips and surgical staples (hereinafter "clips") may be applied using any of a number of tools known in the art. Generally, such a tool includes opposed jaws which crimp the U-shaped clip flat across the tissues to be sutured or tied off. Normally, the tool or applicator that is used to dispense such clips is capable of dispensing a plurality of clips that are fed serially to the jaws.

In most of the tools currently used to dispense such clips, a compression spring is used to supply the force needed to advance the clips in queue towards the jaws until the endmost clip is in position to be dispensed. Although a compression spring generally supplies adequate force to advance the clips toward the jaws in the existing tools, one disadvantage of using a compression spring is that a compression spring occupies a relatively large amount of space within the tool. The tool space that currently is used to house a compression spring could be used more advantageously to hold additional clips. The added clip capacity would reduce the number of times that the tool would have to be reloaded during surgery or other traumatic medical care.

Another disadvantage of using a compression spring to advance the clips toward the jaws is that the amount of force exerted by a compression spring on a queue of clips is not uniform. For example, the pressure that a compression spring exerts on the first clip dispensed from a queue of forty clips will be much greater than the pressure exerted by that same compression spring on the thirty-fifth or fortieth clip in queue. When the first clip in queue is dispensed, thirty-nine other clips maintain the compression spring in a compressed state. The pressure exerted by a highly compressed spring on the first few clips in queue could cause the legs of those first clips to spread during dispensing. This spreading of the legs could prevent the first clip(s) from feeding smoothly into the jaws of applicator.

In contrast, by the time that the thirty-fifth or fortieth clip in queue is dispensed, very few clips remain in queue to maintain the compression spring in its compressed state. In a relatively decompressed state, a compression spring cannot exert the same amount of pressure on the thirty-fifth or fortieth clip in queue as it exerts on the first clip in queue. In fact, the pressure exerted by a compression spring on the last clip(s) in queue may be insufficient to permit those clips to be dispensed from the queue at all.

It therefore would be advantageous to provide an applicator with a means to exert substantially constant pressure on all of the clips in queue. It also would be advantageous to reduce the amount of space required to house the mechanism used to supply such constant pressure.

In addition, it recently has been discovered that clips having a rough or abrasive surface may have enhanced gripping ability and/or may promote tissue in-growth, which helps to hold the clip in place and also promotes healing. Thus, it sometimes is advantageous to coat the clips that will be dispensed by such an applicator with a rough or abrasive material.

However, it also has been discovered that rough or abrasive clips tend to adhere more tightly to one another in queue. In fact, when an applicator is used to dispense abrasive clips, the endmost clip often clings so tightly to the legs of the adjacent clip that the endmost clip cannot be dispensed. The result is a clogged applicator, which is useless until the clog is freed. Of course, clogging of an applicator during traumatic medical care is extremely undesirable.

It therefore would be advantageous to provide an applicator with a means for more effectively disengaging an endmost clip from a column of rough or abrasive clips.

SUMMARY OF THE INVENTION

The present invention provides a simple and inexpensive means to apply a substantially constant force to clips in queue within an applicator. The present invention also provides a means to more effectively dispense the endmost clip from a column of rough or abrasive clips within an applicator.

Generally, the means for applying constant force comprises a constant force spring which is movably secured at both ends within an aperture in the applicator. One end of the spring is secured to a feeder which is movably situated within the aperture below the clips in queue so that, when the endmost clip in queue is dispensed, the feeder forces the dispensed clip into the jaws of the applicator to be crimped. The other end of the constant force spring is movably situated within the aperture adjacent to the end of the queue which is farthest from the jaws so that it exerts a constant pressure which forces the clips in queue towards the jaws of the applicator.

It is not necessary to leave enough space in the applicator to house and to permit longitudinal compression and decompression of a compression spring. Therefore, using the constant force spring of the present invention, space that normally would be occupied by a compression spring instead may be used to house additional clips in queue. In addition, the problem that is experienced with compression springs—too much pressure exerted when the first clips in queue are dispensed and too little pressure exerted when the last clips in queue are dispensed—is avoided because the constant force spring of the present invention exerts substantially the same amount of pressure in dispensing every clip in queue.

The present invention provides a means to dispense an endmost abrasive clip generally comprising a cantilever spring of unique design that (1) applies pressure to the endmost clip in queue so that the endmost clip disengages from the column, and (2) prevents the second endmost clip in queue from being dispensed until after the endmost clip in queue has been dispensed, forced into the jaws, and applied.

In a preferred embodiment, the cantilever spring of the present invention has four contiguous segments. The first segment is adapted to be secured to the applicator housing. The second segment extends away from the first segment and the housing at an angle. The third segment tilts toward the first segment and the housing somewhat so that the angle between the third segment and the first segment is less than the angle between the first segment and the second segment. The fourth and final segment of the cantilever spring is a cam. The third segment actually applies the force needed to dispense the endmost clip in queue. The second and third segments apply the force needed to prevent the second endmost clip from being dispensed until after the endmost clip is dispensed.

Each of the foregoing features can be provided independently in a clip applicator; however, a preferred embodiment includes both of the foregoing features.

BRIEF DESCRIPTION OF THE DRAWINGS

FIG. 1 is cross sectional view of the cantilever spring of the present invention.

FIG. 2 is a plan view of the cantilever spring of FIG. 1.

FIGS. 3-5 are cross sectional views of the cantilever spring of FIGS. 1 and 2 at various stages of operation.

DESCRIPTION OF A PREFERRED EMBODIMENT

Figure 6:
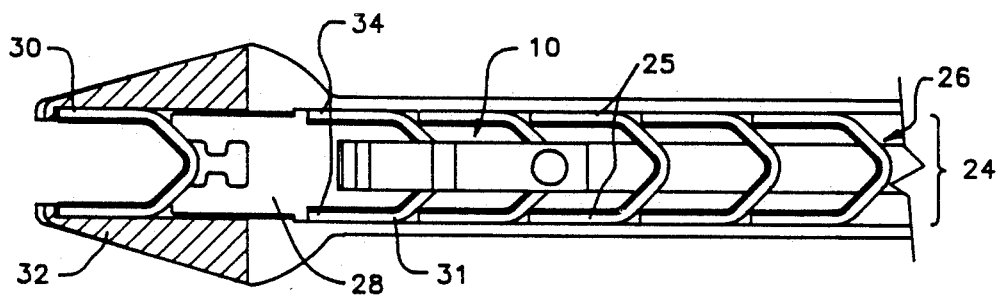
FIG. 6 is an enlarged plan view of the cantilever spring contained in FIGS. 3-5 within the tool housing.

The features of the present invention can be used with any number of clip applicators that are adapted to store, dispense, and crimp a plurality of clips serially, singly, and completely. For example, both of the features of the present invention can be used in the applicator described in U.S. Pat. No. 5,147,038, incorporated herein by reference. A preferred embodiment of the present invention is described in connection with the following figures.

DISPENSING MEANS

The dispensing means of the present invention will be described first. With reference to FIG. 1, the means for dispensing an abrasive clip from a column of such clips within an applicator comprises a spring 10 which is a continuous metal strip having four segments. In a preferred embodiment, spring 10 is a cantilever spring having a first segment 12 which is substantially flat and which includes means to secure the cantilever spring 10 to the tool housing. In the illustrated embodiment, the securing means is an aperture 14, depicted more clearly in FIG. 2, which is adapted to receive a portion of the tool housing. One skilled in the art will appreciate that any number of suitable means may be used to secure the spring 10 to the tool housing.

The second segment 16 of the cantilever spring 10 extends counter-clockwise away from the first segment 12 at an angle beginning at a transition point 13. The third segment 18 angles clockwise back up toward the second segment 16 so that the angle between the third segment 18 and the first segment 12 is substantially smaller than the angle between the second segment 16 and the first segment 12. A transition point 17 is formed between the second segment 16 and the third segment 18. The fourth segment 20 is a cam which also extends at an angle counter clockwise away from the first segment 12 and counter clockwise from the third segment 18 beginning at another transition point 17.

The dimensions of the four segments of the cantilever spring determine the force that will be applied by the spring 10 to dispense the endmost clip in queue. In order to discuss the force that the spring must exert in the present invention, it will be helpful to describe the relevant portions of the clip applicator.

FIG. 3 illustrates the cantilever spring 10 contained within a suitable applicator. As already explained, any number of suitable applicators may be used. The applicator depicted in FIG. 3 includes a housing portion 22 with an chamber 24 therein. A queue of clips 26 is contained within the chamber. The applicator includes means for moving the clips in queue 26 within the chamber. Although the chamber depicted herein is substantially linear, one of skill in the art will recognize that the invention described herein also applies to applicators in which the chamber or the queue of clips 26 is non-linear, e.g., curved.

In a preferred embodiment, the means for moving the clips in queue 26 includes a feeder 28 positioned adjacent to the column of clips 26. In FIG. 3, the feeder 28 already has forced a clip 30 into the jaws 32 which are capable of crimping and applying the clip 30 as desired. In FIG. 6, feeder 28 clearly can be seen holding a clip 30 within the jaws 32 in preparation for crimping.

The spring 10 should be small enough to fit within the chamber 24 in the housing 22 and between the legs 25 (FIG. 6) of the clips 26, but strong enough to disengage the endmost clip 31 of the clips in queue 26 and to prevent the remaining clips in queue 26 from lifting the spring 10 when the feeder 28 is retracted from under the endmost clip 31. The spring 10 also should be pliable enough so that the feeder 28 can lift the spring 10 when the feeder 28 is forced forward to feed the endmost clip 31 into the jaws 32 of the tool. The dimensions that affect the strength of the spring 10 include the thickness and width of the strip comprising the spring 10, the length and height of the four segments of the spring 10, and the type of material from which the spring 10 is made.

One of skill in the art will recognize that applicators having the features of the present invention may be used to apply clips of many dimensions. The following is a description of an applicator which is useful in applying clips 26 having a thickness of 0.029" with a tolerance of 0.002", and a distance between the two legs 25 of 0.150" with a tolerance of 0.002". The thickness and width of the sheet of material used to form the spring 10 depends upon the material chosen. In the described embodiment, raw stock 300 series stainless steel having a material thickness of about 0.008" with a tolerance of 0.001" was used; however, other materials having similar properties also may be used, such as 400 series heat treated stainless steel, or plastics, such as polycarbonate.

The length 11 (FIG. 1) of the first segment 12 is not critical to the present invention, and depends primarily upon the size of the mounting surface. All that is required is that the length 11 be sufficient to secure the spring 10 to the housing 22 within the dimensions of the chamber 24. In the embodiment described herein, the length 11 of the first segment 12 is 0.25" with a tolerance of approximately 0.010".

The second segment 16 should have a length 16a and height 16b sufficient to maintain the first segment 12 above the clips in queue 26. The angle at which the second segment 16 extends away from the first segment 12 determines where the cantilever spring 10 flexes when the cam 20 is pushed upwards by the feeder 28. It is desirable for the cantilever spring 10 to flex at the transition point 13. In the embodiment described herein, the length 16a of the second segment 16 is 0.055" with a tolerance of 0.010". The height 16b of the second segment 16 is 0.050", also with a tolerance of 0.010". The angle at which the second segment 16 extends away from the first segment 12 is a function of the length 16a and height 16b of the second segment 16. In the described embodiment, the angle measured counter clockwise from the first segment 12 could range between 49°-59°, but preferably is approximately 54°.

The half of the third segment 18 which is closest to the second segment 16 prevents the remaining clips in queue 26 from being dispensed until after the endmost clip 31 is dispensed and applied. The length 18a of the third segment 18 may be adjusted so that the cantilever spring 10 will operate with clips 26 of varying lengths. The height 18b of the third segment 18 determines where the endmost clip 31 will stop before the feeder 28 is re-extended under the column of clips 26 to begin a new cycle. The height 18b of the third segment 18 also determines the minimum load required to lift the cantilever spring 10 and the maximum load that will be applied to the clips in queue 26. In the illustrated embodiment, the length 18a is 0.100", with a tolerance of 0.010", and the height 18b is 0.013" with a tolerance of 0.005". Once again, the angle between the third segment 18 and the first segment 12 is a function of the length 18a and the height 18b of the third segment. In the illustrated embodiment, that angle measured counter clockwise from the first segment 12 ranges between 3°-13°, but preferably is approximately 8°.

The cam 20 may be V-shaped or U-shaped, as shown, or may take various forms. For example, the cam 20 may simply terminate at the bottom edge. The height 20b of the cam 20 determines how high the cantilever spring 10 will be deflected by the feeder 28. It is important for the third segment 18 of the cantilever spring 10 to clear the top of the endmost clip 31 by at least 0.001". In the illustrated embodiment, the height of deflection 18b is 0.047", with a tolerance of 0.005". The width 20a of the cam 20 may vary with the shape of the cam. The width of the illustrated embodiment is approximately 0.030".

It would be a matter of routine skill to determine the adjustments that should be made to the described dimensions of the second, third and fourth segments (16, 18, and 20) of the cantilever spring 10 in order to accommodate clips 26 of different dimensions.

The spring 10 of the present invention operates in three stages. The first stage is depicted in cross section in FIG. 3 and in plan view (with the top of the tool housing removed) in FIG. 6. In the first stage, the feeder 28 has been forced forward and a clip 30 is loaded into the jaws 32 for crimping. The spring 10 is cammed up above the clips in queue 26 by the feeder 28, which extends under the cam 20 of the spring 10. The legs 34 of the endmost clip 31 abut an inclined surface 36 of the tool housing.

In the second stage, shown in FIG. 4, the spring 10 rotates downward as the feeder 28 is retracted from underneath the cam 20. As the feeder 28 is retracted, the third segment 18 of the spring 10 forces the apex 38 of the endmost clip 31 downward until it reaches the cam 20. As the downward force exerted by the cantilever spring 10 forces the apex 38 of the clip 31 downward along the third segment 18, the downward pressure exerted by the third segment 18 dispenses the endmost clip 31 from the clips in queue 26 and places the endmost clip 31 in front of the feeder 28. The remaining clips in queue 26 advance until the apex 43 of the next endmost clip contacts the transition point 17 between the second segment 16 and the third segment 18 of the spring 10. The contact between the apex 43 of the next endmost clip and the third segment 18 of the spring 10 prevents the next endmost clip 42 from advancing further until after the endmost clip 31 is crimped and the feeder 28 is forced forward again underneath the column of clips 26 and the cam 20.

In FIG. 5, the feeder 28 has advanced forward to load the endmost clip 31 into the jaws 32. The pressure of the feeder 28 on the cam 20 forces the spring 10 upward, thereby allowing the next endmost clip 42 to advance until it is caught and held in position by the third segment 18. The entire cycle then may be repeated.

CONSTANT FORCE MEANS

The means for apply a substantially constant force to the clips in queue 26 now will be described.

Figure 7:
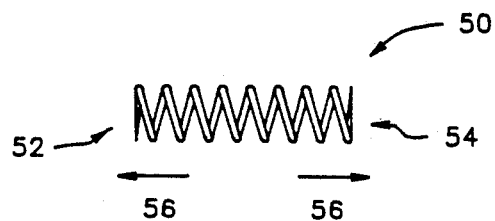
FIG. 7 is a plan view of a typical compression spring.

FIG. 7 illustrates a typical compression spring 50 similar to those used in most existing clip applicators. The force exerted by such a spring 50 is created by compressing the distal end 52 and the proximal end 54 together. The natural tendency of a compression spring 50 is to decompress, thereby exerting pressure outwardly toward the ends of the spring, as indicated by the arrows 56.

Figure 8:
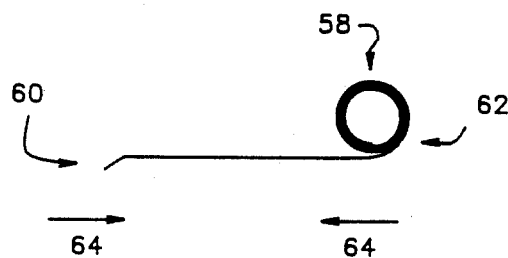
FIG. 8 is a cross sectional view of a constant force spring suitable for use in the present invention.

FIG. 8 represents a typical constant force spring 58 suitable for use in the present invention. The constant force spring 58 also has a distal end 60 and a proximal end 62. In contrast to a compression spring 50, however, the ends 60, 62 of a constant force spring 58 naturally are drawn toward one another in the direction shown by the arrows 64.

Constant force springs 58 are known in the art. In constructing the embodiment described herein, the inventors obtained a constant force spring having the following specifications from Vulcan Spring & Manufacturing Co., 501 Schoolhouse Road, Teleford, Pa. 18969. A similar constant force spring 58 can be obtained from other commercial sources.

The load of a constant force spring 58 is determined by a number of parameters, including the type of material used, the material thickness, and the inside and outside diameter of the spring. The parameters chosen for the constant force spring 58 of the present embodiment were: type 301 stainless steel with a material thickness of 0.0015" and a tolerance of 0.0003"; a maximum outside diameter of 0.155"; a standard spring width of 0.062" (designated 26 in FIG. 4); and, a spring length of 6.5" with a tolerance of 0.05". One of skill in the art will recognize that the foregoing dimensions may be varied for application to different hemostatic clip applicators.

Figure 9:
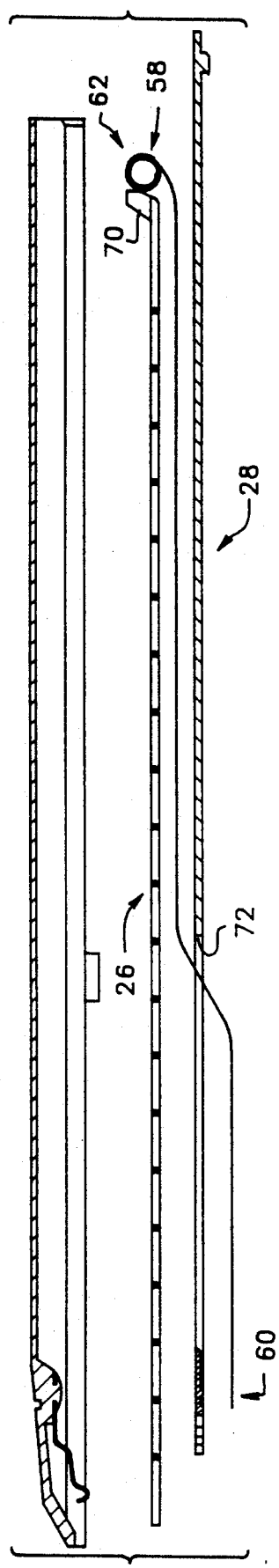
FIG. 9 is an exploded cross sectional view of a constant force spring housed within a hemostatic clip applicator.

FIG. 9 illustrates the elements of a clip applicator that interact with the constant force spring 58 of the present invention. The clips in queue once again are designated 26. In the illustrated embodiment, a clip pusher 70 is provided at the proximal end of the column. The proximal end 62 of the constant force spring 58 abuts the pusher 70.

One of skill in the art will recognize that a pusher 70 is not a required element of the present invention. All that is required is that the constant force spring 58 be in mechanical communication with or be capable of exerting pressure to move the clips in queue 26.

Figure 10:
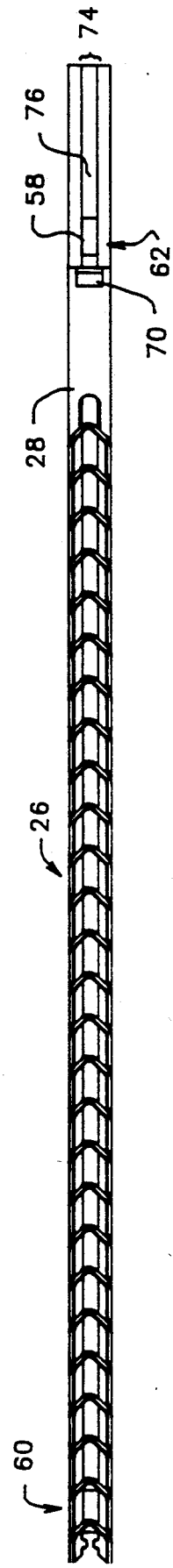
FIG. 10 is a plan view of a constant force spring housed within a hemostatic clip applicator.
Figure 11:
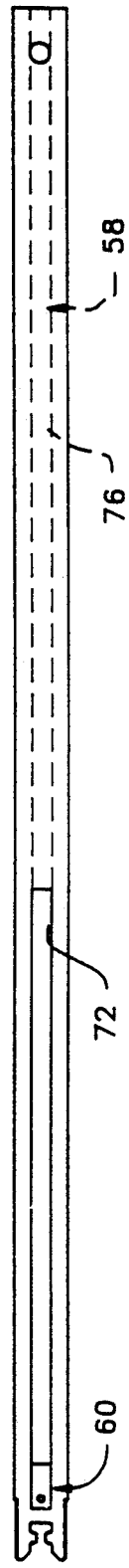
FIG. 11 is a plan view of a feeder adapted for use with the constant force spring of the present invention.

In the illustrated embodiment, a feeder 28 is provided having a slot 72, also shown in plan view in FIG. 11, through which the distal end 60 of the constant force spring 58 is inserted. Once inserted through slot 72, the distal end 60 of the constant force spring 58 can be attached to the feeder 28 by conventional means. FIG. 10 is simply a plan view of FIG. 9 illustrating that the width 74 of the constant force spring 58 is small enough to fit within a groove 76 on the feeder 28. FIG. 10 also illustrates how the pusher 70 abuts the column of clips 26.

One of skill in the art will recognize that many means may be used to establish mechanical communication between the feeder 28 and the distal end 60 of the constant force spring 58. For example, the constant force spring 58 may be provided with an aperture adapted to engage a post or other protrusion extending from the feeder 28. The particular means for establishing mechanical communication between the distal end 60 of the constant force spring 58 and the feeder 28 is not critical to the present invention.

Figure 12:
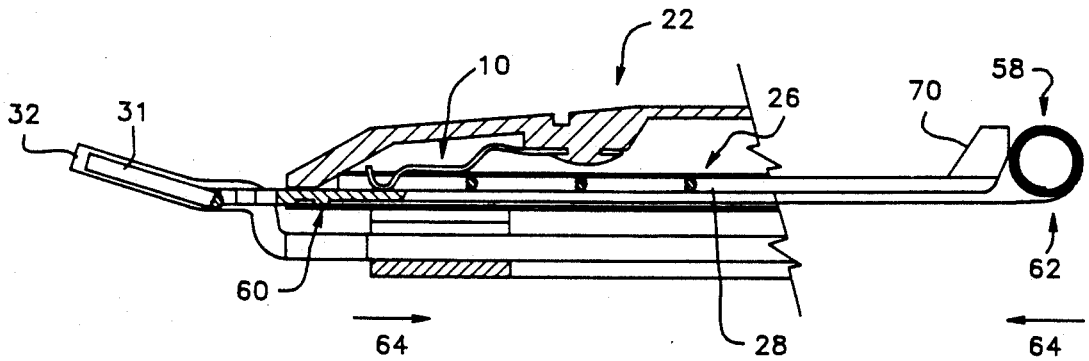
FIG. 12 is a cross sectional view of a preferred embodiment of the present invention including both the cantilever spring and the constant force spring of the present invention.

The operation of the constant force spring 58 will be described with reference to a preferred embodiment, shown in FIG. 12, in which the constant force spring 58 of the present invention is used in conjunction with the cantilever spring 10 of the present invention. Briefly, the inward force 64 of the constant force spring 58 causes the proximal end 62 of the constant force spring 58 to apply pressure to the pusher 70 which forces the clips in queue 26 forward toward the jaws 32 of the applicator. The endmost clip 31 is dispensed from the clips in queue 26 by the cantilever spring 10 and forced by the feeder 28 into the jaws 32. After the clip has been crimped and applied to a blood vessel, the entire cycle may be repeated.

The constant force spring 58 of the present invention is particularly advantageous for use with abrasive clips because the interaction of the two movable ends 60, 62 creates a jogging action which helps to counteract any frictional force that exists between adjacent clips in queue 26.

One of skill in the art will appreciate that many modifications may be made to the embodiment described herein and depicted in the accompanying drawings without departing from the spirit of the present invention. Accordingly, the embodiment described herein is illustrative only and is not intended to limit the scope of the present invention.

What is claimed is:

1. An applicator device for storing, dispensing, and applying a plurality of clips in serial fashion, comprising:
   a tool housing surrounding a chamber for storing a plurality of clips in column fashion;
   jaw means connected to said tool housing for applying said clips;
   feeder means for feeding said clips into said jaw means;
   dispensing means for selectively dispensing an endmost clip from said column of clips in serial, sequential fashion;
   said dispensing means further comprises a spring which further comprises
      a first segment adapted to be secured to said tool housing,
      a second segment contiguous with said first segment and extending at a first angle away from said first segment,
      a third segment contiguous with said second segment and extending away from said first segment in the same direction as said second segment but at a second angle that is smaller than said first angle,
      a fourth segment contiguous with said third segment comprising a cam; and
   a constant force spring having two ends movably contained within said tool housing, one end of said spring being in mechanical communication with said column and the other end of said spring being in mechanical communication with said feeder means, whereby a substantially constant force is applied to said column to move said column within said chamber.

2. A method for moving a column of clips within a chamber in an applicator comprising:
   temporarily supporting said column of clips in said chamber with a feeder;
   moving said endmost clip toward jaws for applying said clips using a constant force spring having two ends movably contained within said chamber, one end of said spring being in mechanical communication with said column and the other end of said spring being in mechanical communication with said feeder, whereby a substantially constant force is applied to said column to move said column within said chamber;
   applying pressure against said endmost clip to position said endmost clip between said feeder and said jaws using a spring comprising a first segment adapted to be secured to a tool housing, a second segment contiguous with said first segment and extending at a first angle away from said first segment, a third segment continuous with said second segment and extending away from said first segment in the same direction as said second segment but at a second angle that is smaller than said first angle, and a fourth segment, comprising a cam, contiguous with said third segment;
   retracting said feeder from said endmost clip in said column whereby said support is withdrawn from said endmost clip; and
   dispensing said endmost clip.

* * * * *